(12) United States Patent
Kikuchi et al.

(10) Patent No.: US 7,511,186 B2
(45) Date of Patent: Mar. 31, 2009

(54) ABSORBENT ARTICLE WITH DISPLACE ELEMENT BETWEEN BACKSHEET AND ABSORBENT CORE

(75) Inventors: Kyo Kikuchi, Kagawa-ken (JP); Yoshitaka Mishima, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 224 days.

(21) Appl. No.: 11/188,867

(22) Filed: Jul. 26, 2005

(65) Prior Publication Data

US 2006/0025733 A1 Feb. 2, 2006

(30) Foreign Application Priority Data

Jul. 28, 2004 (JP) .............................. 2004-220165

(51) Int. Cl.
*A61F 13/15* (2006.01)

(52) U.S. Cl. ............. 604/361; 604/385.28; 604/385.29; 604/385.3; 604/385.24; 604/385.25

(58) Field of Classification Search ................. 604/361, 604/385.28, 385.29, 385.3, 385.24, 385.25; D24/126

See application file for complete search history.

(56) References Cited

U.S. PATENT DOCUMENTS 5,219,341 A * 6/1993 Serbiak et al. ............... 604/361
5,766,212 A * 6/1998 Jitoe et al. ................... 604/361
6,297,424 B1 * 10/2001 Olson et al. ................. 604/361
6,747,185 B2 * 6/2004 Inoue et al. ................. 604/361
2001/0044611 A1 * 11/2001 Noda et al. .................. 604/367

FOREIGN PATENT DOCUMENTS

| EP | 0 813 850 A2 | 12/1997 |
| JP | 57-167709 | 4/1982 |
| JP | 58-121305 | 8/1983 |
| JP | 60-75402 | 5/1985 |
| JP | 61-33810 | 3/1986 |
| JP | 1997-140742 | 6/1997 |

* cited by examiner

*Primary Examiner*—Jacqueline F. Stephens
(74) *Attorney, Agent, or Firm*—Lowe, Hauptman, Ham & Berner, LLP

(57) ABSTRACT

An absorbent article such as a disposable diaper is provided with an indicator adapted to become visible as soon as bodily fluid is discharged. The indicator includes a composite nonwoven fabric composed of a hydrophilic melt blown nonwoven fabric layer and a hydrophilic spun bond nonwoven fabric layer on which a display element is depicted and laminated on one surface of the hydrophilic melt blown nonwoven fabric layer. A first surface of the composite nonwoven fabric facing an absorbent core of the diaper is held together with the display element and a second surface of the composite nonwoven fabric facing a backsheet of the diaper is held in close contact with the inner surface of the backsheet.

20 Claims, 9 Drawing Sheets

ABSORBENT ARTICLE WITH DISPLACE ELEMENT BETWEEN BACKSHEET AND ABSORBENT CORE

RELATED APPLICATIONS

The present application is based on, and claims priority from, Japanese Application Number 2004-220165, filed Jul. 28, 2004, the disclosure of which is hereby incorporated by reference herein in its entirety.

BACKGROUND OF THE INVENTION

This invention relates generally to an absorbent article such as a disposable diaper and an infant's toilet training pant provided with an indicator allowing a parent or a care personnel of a wearer to perceive whether bodily fluids have been discharged or not.

There have already been proposed disposable diaper comprising a liquid-pervious topsheet, a light-transmissive and liquid-impervious backsheet and a liquid-absorbent core interposed between these sheets, wherein the diaper is provided between the backsheet and the core with an indicator adapted to make discharge of bodily fluids visible when the indicator is wetted with bodily fluids. The diaper is disclosed, for example, in Japanese Unexamined Patent Application Publication No. 1997-140742 (hereinafter referred to as "Reference"). The indicator has a belt-like shape which is relatively long in a transverse direction and extends in the transverse direction in a longitudinal midsection of a front waist region.

The indicator comprises a base sheet made of paper, a first coating layer intermittently laid on the inner surface of the base sheet facing the core and a while or milky white second coating layer intermittently laid on the outer surface of the base sheet facing the backsheet. The first coating layer has a color tone different from those of the backsheet, the base sheet and the second coating layer and contains light scattering materials such as silica or alumina in the form of microscopic particles. The second coating layer also contains light scattering materials such as silica or alumina in the form of microscopic particles and utilizes diffused reflection of light to cover up the first coating layer. When bodily fluids discharged on the diaper put on the wearer's body permeate the first and second coating layers, light scattering in both the first and second coating layers is so reduced that the effect to cover up the first coating layer is deteriorated. Consequentially, the first coating layer becomes visible through the base sheet and the second coating layer from the outside of the backsheet. In this way, the parent or the care personnel can visually determine from the outside of the backsheet whether bodily fluids have been discharged or not on the diaper.

In the case of the diaper disclosed in Reference, bodily fluids having been absorbed by the core permeate the first coating layer and then the base sheet and thereafter permeate the second coating layer from the base sheet. In other words, a certain time is taken before bodily fluids having been discharged on the diaper reach the second coating layer. In addition, no capillary action occurs in the second coating layer and it is difficult for the second coating layer to absorb bodily fluids at once. Even after bodily fluids have reached the second coating layer, a certain time is taken before the light scattering in the second coating layer is significantly reduced. Consequentially, it is always likely that the parent or the care personnel might not perceive discharge of bodily fluids immediately after it has occurred since a certain time is taken until the first coating layer becomes visible after bodily fluids have been discharged.

SUMMARY OF THE INVENTION

It is an object of this invention to provide an absorbent article provided with an indicator allowing the parent or the care personnel to perceive discharge of bodily fluids immediately after it has occurred.

According to this invention, there is provided an absorbent article comprising a liquid-pervious topsheet, a light transmissive and liquid-impervious backsheet and a liquid-absorbent core interposed between these sheets and an indicator disposed between the backsheet and the core and allowing discharge of bodily fluids to be visible from an outside of the backsheet when the indicator is wetted with bodily fluids.

The article according to this invention further comprises the indicator comprising a hydrophilic fibrous nonwoven fabric and a display element depicted on the hydrophilic fibrous nonwoven fabric so that the hydrophilic fibrous nonwoven fabric covers up the display element so long as the hydrophilic fibrous nonwoven fabric is in a dry state and allows the display element to be visible through the hydrophilic fibrous nonwoven fabric from the outside of the backsheet when the hydrophilic fibrous nonwoven fabric absorbs bodily fluids.

This invention described above may include as follows:

The hydrophilic fibrous nonwoven fabric comprises one of a hydrophilic melt blown nonwoven fabric layer and a hydrophilic spun bond nonwoven fabric layer. The display element is depicted on a first surface of the hydrophilic fibrous nonwoven fabric facing the core, the first surface of the hydrophilic fibrous nonwoven fabric is held together with the display element in close contact with the surface of the core, and a second surface of the hydrophilic fibrous nonwoven fabric facing the backsheet is held in close contact with an inner surface of the backsheet.

The hydrophilic fibrous nonwoven fabric comprises a hydrophilic melt blown nonwoven fabric layer and a hydrophilic spun bond nonwoven fabric layer and laminated on at least one surface of the melt blown nonwoven fabric layer. The display element is depicted on a first surface of the hydrophilic fibrous nonwoven fabric facing the core, the first surface of the hydrophilic fibrous nonwoven fabric is held together with the display elements in close contact with the surface of the core, and a second surface of the hydrophilic fibrous nonwoven fabric facing the backsheet is held in close contact with the inner surface of the backsheet.

The hydrophilic fibrous nonwoven fabric exhibits a total luminous transmittance in a range of 20% to 40% in its dry state and in a range of 60% to 95% when the hydrophilic fibrous nonwoven fabric absorbs bodily fluids.

The hydrophilic fibrous nonwoven fabric contains a hydrophilically modifying agent per unit weight in a range of 0.5% by weight to 5.0% by weight.

The hydrophilic fibrous nonwoven fabric exhibits a Klemm's water absorbency in a range of 1 mm to 90 mm.

The hydrophilic fibrous nonwoven fabric exhibits a water absorption per unit weight in a range of 5% by weight to 600% by weight.

The hydrophilic fibrous nonwoven fabric has a plurality of heat-embossed spots depressed in its thickness direction at an area ratio to unit area of the hydrophilic fibrous nonwoven fabric in a range of 5% to 50% and the display element is depicted so as to occupy a part of the heat-embossed spots as well as a part of a region surrounding the heat-embossed spots.

The display element is formed on the hydrophilic fibrous nonwoven fabric with one of an ink layer and a coating layer.

Urine discharged on the absorbent article of this invention is rapidly absorbed and retained by the hydrophilic fibrous nonwoven fabric defining the indicator under the effect of capillary action whereupon the light scattering on the nonwoven fabric is reduced and the display element having been covered up by the nonwoven fabric in its dry state become visible. Thus the indicator allows the parent or the care personnel to determine from the outside of the backsheet whether bodily fluids have been discharged or not.

In the case of the absorbent article wherein the hydrophilic fibrous nonwoven fabric defining the indicator is formed from the melt blown nonwoven fabric layer made of extrafine fibers, high density and smooth surface of the nonwoven fabric advantageously enhance the cover-up effect of the nonwoven fabric layer for the display element and allow the display elements to be clearly depicted on the nonwoven fabric layer without an anxiety that the display element might exude on the surface of the nonwoven fabric layer. In addition, the melt blown nonwoven fabric layer rapidly absorbs bodily fluids under the effect of capillary action whereupon the light scattering on the nonwoven fabric layer is substantially reduced to ensure that the display element having been covered up by the nonwoven fabric layer in its dry state become clearly visible. In this way, the indicator allows the parent or the care personnel to perceive from the outside of the backsheet an occurrence of bodily fluids' discharge immediately thereafter.

In the case of the absorbent article wherein the hydrophilic fibrous nonwoven fabric defining the indicator is formed from the spun bond nonwoven fabric layer made of continuous fibers, the nonwoven fabric layer exhibits high diffusibility and absorbability for bodily fluids. Consequentially, bodily fluids rapidly spread in the nonwoven fabric layer and are rapidly absorbed by the nonwoven fabric under the effect of capillary action. Thereupon the light scattering on the nonwoven fabric layer is rapidly reduced and the display elements having been covered up by the nonwoven fabric layer in its dry state become visible at once. In this absorbent article, the indicator allows the parent or the care personnel to perceive from the outside of the backsheet an occurrence of bodily fluids' discharge immediately thereafter.

In the case of the absorbent article wherein the hydrophilic fibrous nonwoven fabric defining the indicator is formed from the composite nonwoven fabric composed of the melt blown nonwoven fabric flayer and the spun bond nonwoven fabric layer laminated together, a high cover-up effect of the melt blown nonwoven fabric layer for the display element can be advantageously utilized with a high diffusibility as well as a high absorbability of the spun bond nonwoven fabric layer for bodily fluids. Specifically, the display element can be clearly depicted and bodily fluids can be rapidly absorbed by the indicator. In this absorbent article also, the indicator allows the parent or the care personnel to perceive from the outside of the backsheet an occurrence of bodily fluids' discharge immediately thereafter.

In the case of the absorbent article wherein the hydrophilic fibrous nonwoven fabric exhibits a total luminous transmittance in a range of 20% to 40% when the nonwoven fabric is dry and in a range of 60% to 95% when the nonwoven fabric has absorbed bodily fluids, the display element is reliably covered up by the nonwoven fabric so far as the nonwoven fabric is in a dry state and the display element reliably become visible as soon as the nonwoven fabric has absorbs bodily fluids.

In the case of the absorbent article wherein the hydrophilic nonwoven fabric contains the hydrophilically modifying agent in a range of 0.5% by weight to 5.0% by weight per unit weight of the hydrophilic nonwoven fabric, the nonwoven fabric absorbs bodily fluids at a rate so improved by addition of the hydrophilically modifying agent that the display element can become immediately after bodily fluids have been discharged.

In the case of the absorbent article wherein the hydrophilic fibrous nonwoven fabric exhibits a Klemm's water absorbency in a range of 1 mm to 90 mm, the nonwoven fabric exhibits a rate of absorption as well as a diffusibility for bodily fluids so improved that bodily fluids are rapidly diffused and absorbed in the nonwoven fabric and the display element becomes visible immediately after bodily fluids have been discharged.

In the case of the absorbent article wherein the hydrophilic fibrous nonwoven fabric exhibits a water absorption per unit weight in a range of 5% by weight to 600% by weight, a predetermined amount of bodily fluids can be reliably absorbed by the nonwoven fabric and the display element can become visible immediately after bodily fluids have been discharged.

In the case of the absorbent article wherein the hydrophilic fibrous nonwoven fabric has a plurality of heat-embossed spots depressed in its thickness direction, the part of the display element occupying these heat-embossed spots becomes most clearly visible as soon as the nonwoven fabric absorbs bodily fluids and cooperates with the part of the display element occupying the region having none of the heat-embossed spots to ensure that the display element in entirety can become clearly visible.

DETAILED DESCRIPTION OF THE PREFERRED EMBODIMENTS

Figure 1:
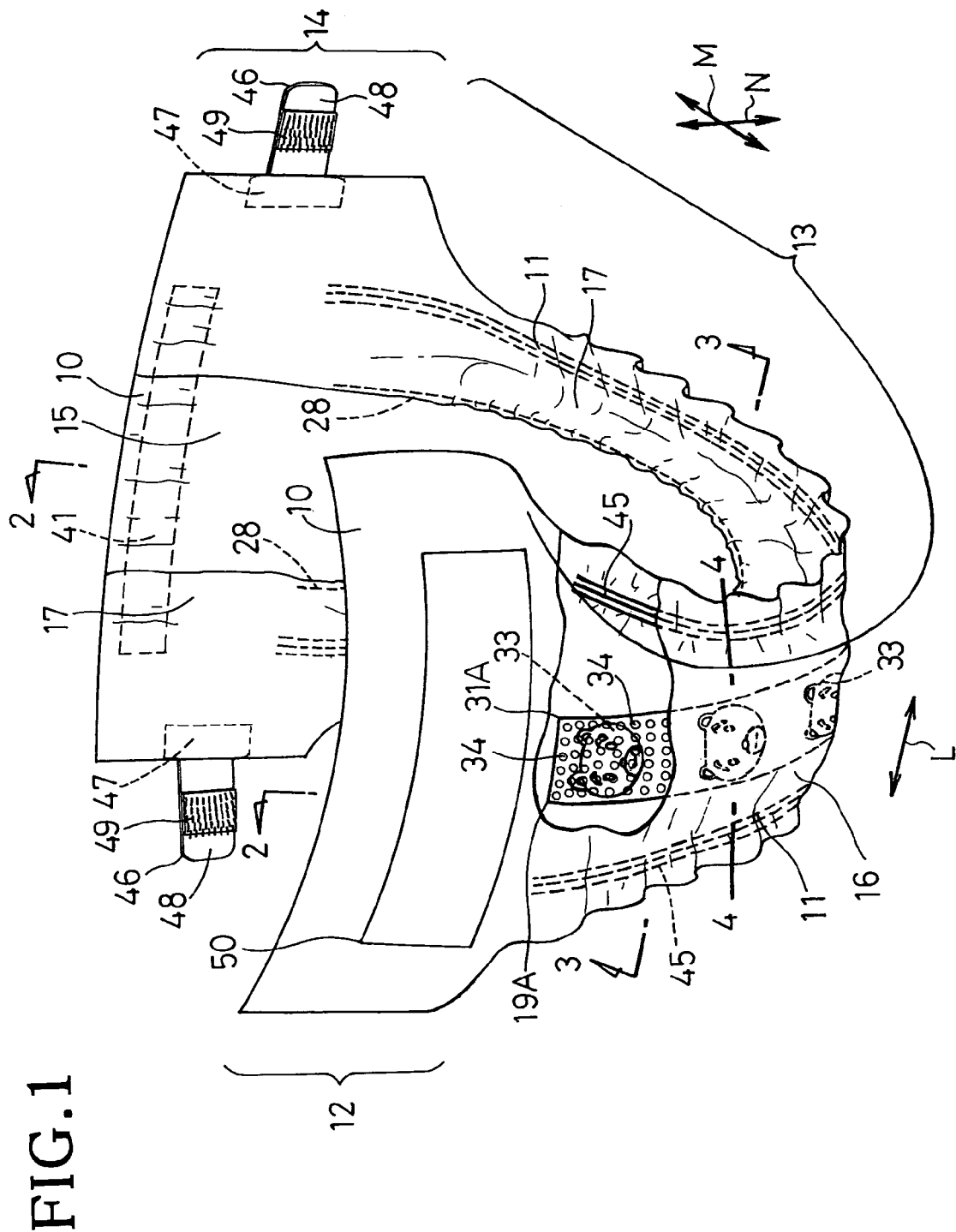
FIG. 1 is a partially cutaway perspective view showing a preferred first embodiment of an absorbent article according to this invention.

Details of a disposable diaper as an example of an absorbent article according to this invention will be more fully understood from the description given hereunder with reference to the accompanying drawings.

Referring to FIG. 1 through FIG. 4 showing a first embodiment of this invention, a diaper is contoured by a pair of ends 10 extending in a transverse direction and a pair of side edges 11 extending in a longitudinal direction. The diaper defines a front waist region 12, a rear waist region 14 and a crotch region 13 extending between these waist regions 12, 14. The diaper comprises a liquid-pervious topsheet 15 facing the wearer's body, a light-transmissive and liquid-impervious backsheet 16 facing a garment, a pair of liquid-impervious leak-barrier cuffs 17 and a liquid-absorbent core 18 interposed between the top- and backsheets 15, 16 and bonded to respective inner surfaces of these sheets 15, 16. The core 16 is laid in the front and rear waist regions 12, 14 as well as in the crotch region 13 leaving the ends 10 and the side edges 11. The side edges 11 of the crotch region 13 describe circular arcs which are convex inward in the transverse direction of the diaper. Thus the diaper has a generally hourglass-like planar shape. Between the backsheet 16 and the core 18, there is provided with an indicator 19A allowing a parent or a care personnel to perceive discharge of bodily fluids from the outside of the backsheet 16.

The topsheet 15 is formed from a hydrophilic fibrous nonwoven fabric 20. The backsheet 16 is formed from a composite sheet composed of a breathable liquid-impervious plastic film 21 facing the core 18 and a hydrophobic fibrous nonwoven fabric 22 laminated on the outer side of the film 21. The leak-barrier cuffs 17 are formed from a water repellency treated hydrophobic fibrous nonwoven fabric 23. Materials for the fibrous nonwoven fabric layers 20, 22, 23 may be selected from those made by processes consisting of spun lace-, needle punch-, melt blown-, thermal bond-, spun bond- and chemical bond-processes. Component fibers of these nonwoven fabric layers 20, 22, 23 may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers.

The film 21 is formed from an oriented plastic film containing microscopic particles of inorganic substances such as silica and alumina. The film 21 is obtained by film extrusion of a clear and colorless thermoplastic synthetic resin containing the microscopic particles of the inorganic substances and then monoaxially or biaxially orienting this film at a predetermined ratio. On the surface of the film 21 obtained in this manner, the particles stand out to form a plurality of microscopic irregularities (not shown). The film 21 assumes white or milky white and has, in addition to a luminous reflectivity and a luminous absorbability, a luminous transmittance. In the dry state, the light incident upon the surface of the film 21 is diffusively reflected and correspondingly the film 21 exhibits a high luminous reflectivity and a low luminous transmittance. However, in the state wetted with bodily fluids, the luminous reflectivity, and therefore the light scattering are reduced and the luminous transmittance is correspondingly enhanced. The film 21 exhibits a total luminous transmittance in a range of 55% to 75% in its dry state and in a range of 65% to 99% in its state wetted with bodily fluids.

While the nonwoven fabric layer 22 assumes white or milky white due to diffused reflection on the component fibers, this nonwoven fabric layer 22 also has a luminous transmittance, in addition to a luminous reflectivity and a luminous absorbability because the incident light can permeate the component fibers themselves and pass the fiber interstices. The nonwoven fabric layer 22 exhibits a total luminous transmittance in a range of 20% to 40% in its dry state and in a range of 60% to 95% in its state wetted with bodily fluids.

The backsheet 16 has its luminous transmittance enhanced as the film 21 constituting the backsheet 16 is wetted with bodily fluids. The backsheet 16 exhibits a total luminous transmittance in a range of 50% to 70% in its dry state and in a range of 55% to 90% in its state wetted with bodily fluids. It is possible without departing from the scope of the invention to form the backsheet 16 using the film 21 alone or using the nonwoven fabric layer 22 alone. It is also possible without departing from the scope of the invention to form the film 21 using a clear and colorless oriented smooth-surface plastic film which contains none of the microscopic particles of the inorganic substances and has a relatively high luminous transmittance.

The core 18 comprises a mixture of particulate or fibrous super-absorbent polymers and fluff pulp fibers or a mixture of particulate or fibrous super-absorbent polymers, fluff pulp fibers and thermoplastic synthetic resin fibers, in both cases, compressed to a desired thickness. The core 18 is entirely wrapped with a liquid-absorption and diffusion sheet 24 such as tissue paper (See FIG. 4) in order to prevent the core 18 from getting out of its initial shape.

The leak-barrier cuffs 17 respectively have proximal sections 25 bonded to the side edges 11 and extending in the longitudinal direction, distal sections 26 extending in the longitudinal direction and normally biased to rise up above the topsheet 15 and ends 27 collapsed inward in the transverse direction of the diaper and bonded in such a collapsed state to the ends 10. Both the proximal sections 25 and the distal sections 26 extend between the ends 10.

The distal sections 26 are provided along its edges with elastic members 28 extending in the longitudinal direction contractibly attached thereto. Specifically, these elastic members 28 are secured to the respective distal sections 26 while these elastic members 28 are stretched in the longitudinal direction at a predetermined ratio. Contraction of the elastic members 28 causes the diaper to curve such that the front and rear waist regions 12, 14 are opposite to each other with the topsheet 15 inside and at the same time causes the distal sections 26 of the leak-barrier cuffs 17 to contract in the longitudinal direction whereupon the distal sections 26 rise up above the topsheet 15 so as to form barriers against bodily discharges. The distal sections 26 rising up in this manner to prevent bodily discharges from leaking sideways.

The indicator 19A is relatively long in the longitudinal direction and is laid in the transverse midsection of the diaper so that the indicator 19A extends over the crotch region 13 further into the front and rear waist regions 12, 14. The indicator 19A is formed from a composite nonwoven fabric 31A composed of a hydrophilic melt blown nonwoven fabric layer 29 and a hydrophilic spun bond nonwoven fabric layer 30 laminated on one surface of the melt blown nonwoven fabric layer 29 and display elements 33 depicted on a first surface 32 of the composite nonwoven fabric 31A facing the core 18 (See FIG. 4). The composite nonwoven fabric 31A assumes white or milky white due to diffused reflection on the component fibers but exhibits, in addition to the luminous reflectivity as well as the luminous absorbability, the luminous transmittance since the incident light can permeate the component fibers themselves and pass the fiber interstices. The composite nonwoven fabric 31A exhibits a high luminous reflectivity and a low luminous transmittance in its dry state because of intensely diffused reflection on the component fibers and, once wetted with bodily fluids, exhibits the luminous transmittance enhanced as the light scattering as well as the luminous reflectivity is reduced.

Of the composite nonwoven fabric 31A, the melt blown nonwoven fabric layer 29 faces the backsheet 16 and the spun bond nonwoven fabric layer 30 faces the core 18. The composite nonwoven fabric 31A is formed with a plurality of heat-embossed spots 34 which are depressed in its thickness direction. At these heat-embossed spots 34, the composite nonwoven fabric 31A are compressed under heating in its thickness direction so that the composite nonwoven fabric 31A may present a substantially film-like state and the melt blown nonwoven fabric layer 29 may be integrated with the spun bond nonwoven fabric layer 30. The melt blown nonwoven fabric layer 29 is bonded to the backsheet 16 (film 21) by means of adhesives 35 intermittently applied to the melt blown nonwoven layer 29 and held in close contact with the backsheet 16. The spun bond nonwoven fabric layer 30 is bonded to the core 18 by means of adhesives 36 intermittently applied to the spun bond nonwoven fabric layer 30 and held in close contact with the core 18. The composite nonwoven fabric 31A has its first surface 32 held together with the display elements 33 in close contact with the surface of the core 18 and its second surface 37 facing the backsheet 16 held in close contact with the inner surface of the backsheet 16.

To form the composite nonwoven fabric 31A, one of the melt blown nonwoven fabric layer 29 and the spun bond nonwoven fabric layer 30 is made and thereafter the other is accumulated on one surface of the one which has been precedently made and is traveling on a net conveyor. In the composite nonwoven fabric 31A, the component fibers of these nonwoven fabric layers 29, 30, respectively, intersect with one another and are fused together at the points of intersection. While details are not shown, after the nonwoven fabric 31A has been made, the nonwoven fabric 31A is guided through a pair of rotary embossing rolls opposed to each other to compress the nonwoven fabric 31A under heating and thereby to form the composite nonwoven fabric 31A with the heat-embossed spots 34. These embossing rolls are formed on peripheral surfaces thereof with a plurality of emboss projections and heated at a predetermined temperature. It should be noted here that it is possible to use the component fibers for the nonwoven fabric layers 20, 22, 23 as the component fibers for the nonwoven fabric layers 29, 30.

The melt blown nonwoven fabric layer 29 has a basis weight in a range of 1 g/m$^2$ to 70 g/m$^2$ and a fiber density in a range of 0.01 g/cm$^3$ to 0.1 g/cm$^3$. The spun bond nonwoven fabric layer 30 has a basis weight in a range of 4 g/m$^2$ to 70 g/m$^2$ and a fiber density in a range of 0.001 g/cm$^3$ to 0.1 g/cm$^3$. The composite nonwoven fabric 31A has a basis weight in a range of 5 g/m$^2$ to 140 g/m$^2$ and a fiber density of 0.011 g/cm$^3$ to 0.2 g/cm$^3$. The composite nonwoven fabric 31A contains a predetermined content of hydrophilically modifying agent.

The display elements 33 are images of bear's face arranged at predetermined intervals in the longitudinal direction and depicted on the spun bond nonwoven fabric layer 30 so that each of these images may occupy a part of the heat-embossed spot 34 as well as a part of the region surrounding the heat-embossed spot 34. The display elements 33 are depicted using aqueous ink of a color tone distinguished from color tones of the backsheet 16 and the composite nonwoven fabric 31A or latex coating of a color tone distinguished from color tones of these backsheet 16 and composite nonwoven fabric 31A. Both these aqueous ink and latex coating may be printed or applied on the composite nonwoven fabric 31A either after or before the formation of the heat-embossed spots 34 on the composite nonwoven fabric 31A.

The ends 10 of the diaper are defined by longitudinally opposite ends 39, 40 of the top- and backsheets 15, 16 extending outward in the longitudinal direction from ends 38 of the core 18 and the ends 27 of the respective leak-barrier cuffs 17. Along the ends 10 of the diaper, the ends 39, 40 of the top- and backsheet 15, 16, respectively are put flat together, the top- and backsheets 15, 16 are bonded together and barrier cuffs 17 are bonded onto the topsheet 15. The end 10 of the rear waist region 14 is provided with strip-like waist elastic member 41 extending in the transverse direction contractibly secured thereto. The waist elastic member 41 is interposed between the end 39 of the topsheet 15 and the end 40 of the backsheet 16 and bonded to respective inner surfaces of these sheets 15, 16 while the elastic member 41 is stretched in the transverse direction at a predetermined ratio.

The side edges 11 of the diaper are defined by side edges 43, 44 of the top- and backsheets 15, 16 extending outward from side edges 42 of the core 18 in the transverse direction and the proximal sections 43 of the respective leak-barrier cuffs 17. Along the side edges 11, the side edges 43 of the topsheet 15 extend outward in the transverse direction slightly beyond the respective side edges 42 of the core 18 and the side edges 44 of the backsheet 16 as well as the proximal sections 25 of the leak-barrier cuffs 17 extend outward in the transverse direction beyond the side edges 43 of the topsheet 15. Along the respective side edges 11, the side edges 43, 44 of the top- and backsheets 15, 16 are put flat together with the proximal sections 25 of the respective leak-barrier cuffs 17, the top- and backsheets 15, 16 have respective inner surfaces bonded together, and the inner and outer surfaces of the top- and backsheets 15, 16, respectively, are bonded to the inner surfaces of the respective leak-barrier cuffs 17. Each of the side edges 11 is provided with a plurality of leg elastic members 45 extending in the longitudinal direction contractibly secured thereto. These leg elastic members 45 are interposed between the respective side edges 44 of the backsheet 16 and the proximal sections 25 of the respective leak-barrier cuffs 17 and bonded to the respective inner surfaces of these sheets 16 and cuffs 17 while the elastic members 45 are stretched in the transverse direction at a predetermined ratio.

The side edges 11 of the rear waist region 14 are provided with tape fasteners 46 made of a plastic film. These tape fasteners 46 respectively have fixed ends 47 and free ends 48 both extending in the transverse direction. The fixed ends 47 are interposed between the side edges 44 of the backsheet 16 and the proximal sections 25 of the leak-barrier cuffs 17 and bonded to respective inner sheets of these sheets 16 and the cuffs 17. The inner surfaces of the respective free ends 48 are provided with male mechanical fasteners 49 comprising a plurality of hooks. It is also possible to coat the inner surfaces of the free ends 48 with pressure-sensitive adhesives, instead of the male mechanical fasteners 49.

The front waist region 12 is provided with a target tape strip 50 on which the free ends 48 of the respective tape fasteners 46 are detachably anchored. The target tape strip 50 comprises a base and a female mechanical fastener defined by a plurality of loops projecting from the base. The target tape strip 50 is shaped in a rectangle being relatively long in the transverse direction and bonded to the outer surface of the backsheet 16. When it is desired to coat the free ends 48 of the tape fasteners 46 with pressure-sensitive adhesives, a plastic film may be used as a suitable material for the target tape strip 50.

Figure 5:
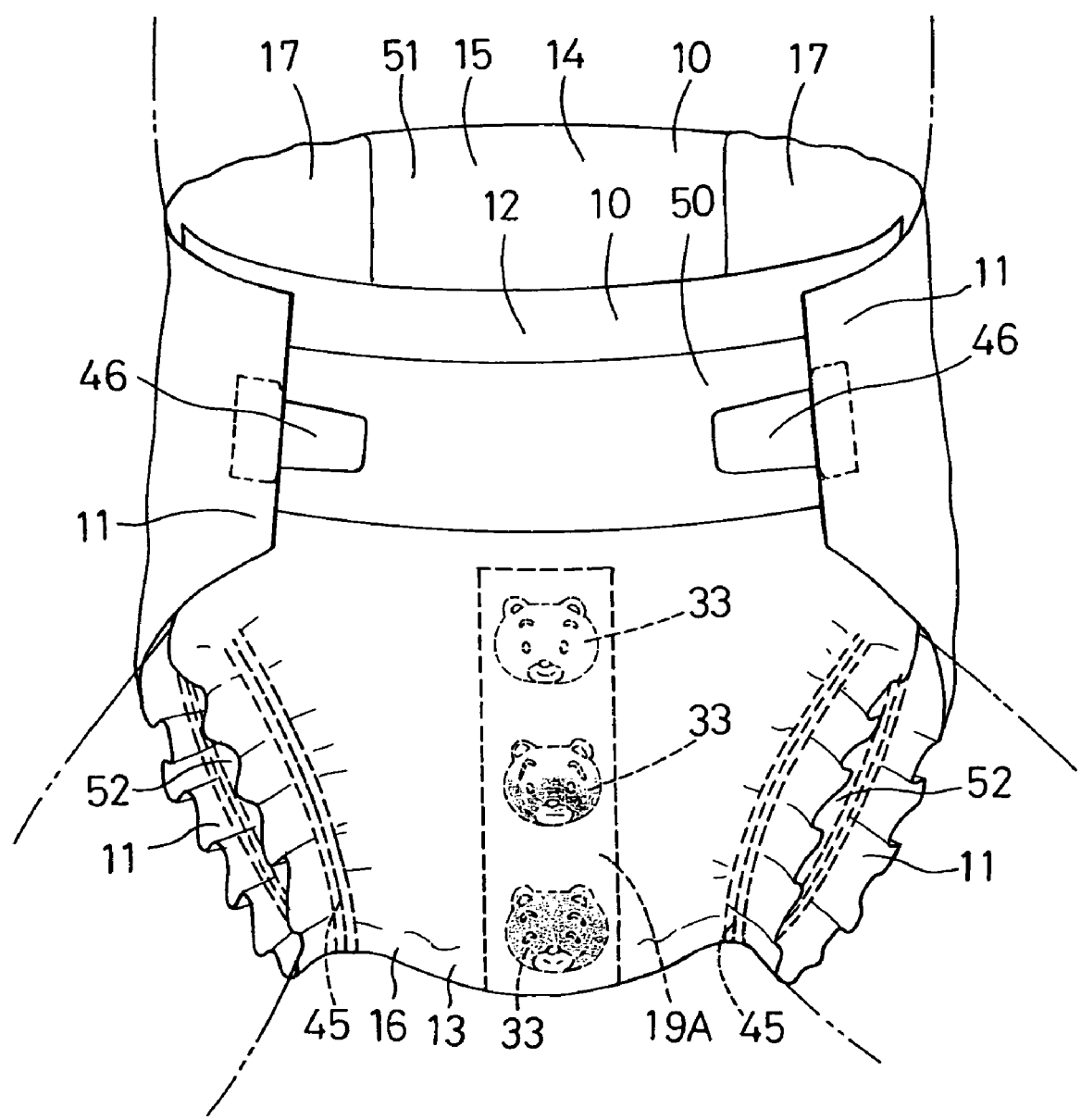
FIG. 5 is a perspective view showing the absorbent article as put on the wearer's body.

FIG. 5 shows a state in which urine has been discharged on the diaper and the display elements 33 have partially become visible. Urine discharged on the diaper put on the wearer's body is absorbed by the core 18 after having permeated the topsheet 15 and, thereafter absorbed by the composite nonwoven fabric 31A defining the indicator 19A.

Until urine is discharged on the diaper, the indicator 19A is in a dry state. The display elements 33 are covered up by the composite nonwoven fabric 31A. Specifically, the display elements 33 are covered up by the melt blown nonwoven fabric layer 29 having a high cover-up effect so that outlines of the respective display elements 33 are faintly visible from the outer side of the backsheet 16 but the parent or the care personnel can not visually recognize each of these display elements 33 in its entirety.

Urine having been discharged on the diaper transfers from the core 18 to the spun bond nonwoven fabric layer 30 and rapidly spreads in the spun bond nonwoven fabric layer 30 in its entirety. At the same time, the melt blown nonwoven fabric layer 29 and the spun bond nonwoven fabric layer 30 rapidly absorb urine under the effect of capillary action and the luminous diffusion in these nonwoven fabric layers 29, 30 is rapidly reduced. Consequentially, the display elements 33 become visible immediately since the luminous transmittance of the nonwoven fabric 31A is correspondingly enhanced and brightness as well as color saturation of the display elements 33 is also enhanced as viewed from the outside of the backsheet 16. In this way, the display elements 33 as a whole can be clearly recognized from the outside of the backsheet 16. The display elements 33 become visible as soon as urine is discharged on the diaper, so that the indicator 19A allows the parent or the care personnel to perceive occurrence of urination from the outside of the backsheet 16 immediately after it has occurred. The backsheet 16 also is wetted with urine as the composite nonwoven fabric 31A is wetted with urine. In other words, the luminous transmittance of the backsheet 16 is enhanced and ensures that the display elements 33 having become visible in entirety thereof can be reliably recognized from the outside of the backsheet 16.

The composite nonwoven fabric 31A includes a plurality of the heat-embossed spots 34 and the display elements 33 are present not only in the region having none of these heat-embossed spots 34 but also in some of these heat-embossed spots 34. Therefore, the display elements 33 become clearly visible not only in the region having none of the heat-embossed spots 34 but also in the heat-embossed spots 34 as the nonwoven fabric 31A absorbs bodily fluids. In this way, the display elements 33 become clearly visible in entirety thereof.

The composite nonwoven fabric 31A exhibits a total luminous transmittance in a range of 20% to 40% in its dry state and in a range of 60% to 95% in its wetted state. If the total luminous transmittance of the composite nonwoven fabric 31A in its dry state exceeds 40%, the composite nonwoven fabric 31A will no more have a desired cover-up effect for the display elements 33 and the brightness as well as the color saturation of the display elements 33 as viewed from the outside of the backsheet 16 will not sufficiently change between in the dry state and in the wetted state of the nonwoven fabric 31A to ensure that the indicator 19A can clearly indicate whether urine has been discharged or not. If the total luminous transmittance of the composite nonwoven fabric 31A in its wetted state is less than 60%, the nonwoven fabric 31A will maintain a relatively high cover-up effect for the display elements 33 even after the nonwoven fabric 31A has absorbed urine and it may be impossible for the parent or the care personnel to see the display elements 33 clearly through the nonwoven fabric 31A from the outside of the backsheet 16 and to perceive that urine has been discharged. The total luminous transmittance of the nonwoven fabric 31A in its dry state and in its wetted state was measured by a method as follows:

(1) Samples of the same nonwoven fabric as the composite nonwoven fabric 31A were prepared (each dimensioned to be 40 mm×40 mm). As the instrument for measurement of the total luminous transmittance, the flicker photometric calorimeter (manufactured by Nippon Denshoku Industries Co., Ltd.) was used.

(2) First, the total luminous transmittance of the sample in its dry state was measured. After zero adjustment (measurement without a stand and the like: light transmitted at 100% was blocked by blackboard so as to achieve a transmittance of 0%), the sample in its dry state was placed on the stand and a TT value (luminous transmittance %) was measured. The TT value measured in this manner was employed as the total luminous transmittance of the sample in its dry state. The TT value was in a range of 20% to 40%.

(3) Then the total luminous transmittance of the sample in its wetted state was measured. After the sample had been immersed in a laboratory dish filled with water (for 1 minute), the sample wetted with water was placed on the stand and a TT value (luminous transmittance %) of the sample was measured. The TT value measured in this manner was employed as the total luminous transmittance of the nonwoven fabric 31A in its wetted state. The TT value was in a range of 60% to 95%.

A content of hydrophilically modifying agent contained in the composite nonwoven fabric 31A (the melt blown nonwoven fabric layer 29+the spun bond nonwoven fabric layer 30) is in a range of 0.5% by weight to 5.0% by weight per unit weight of the nonwoven fabric 31A. If the content of the hydrophilically modifying agent per unit weight of the composite nonwoven fabric 31A is less than 0.5% by weight, hydrophilicity of the nonwoven fabric 31A will be insufficient to ensure that the nonwoven fabric 31A can rapidly absorb urine and thereby to make the display elements 33 visible immediately after urine has been discharged. The hydrophilically modifying agent may be applied on peripheral surfaces of the respective component fibers of the composite nonwoven fabric 31A (the melt blown nonwoven fabric layer 29 +the spun bond nonwoven fabric layer 30) or impregnated into the component fibers of the composite nonwoven fabric 31A (the melt blown nonwoven fabric layer 29+the spun bond nonwoven fabric layer 30). The hydrophilically modifying agent may be selected from a group consisting of anionic surface active agent, cationic surface active agent, nonionic surface active agent and ampholytic surface active agent.

The ink or the coating may contain, in addition to microscopic particles of light scattering inorganic substance such as silica or alumina, the hydrophilically modifying agent similar to that contained in the nonwoven fabric 31A. The ink or the coating may contain also hydrophilic acrylic binder. When the ink or the coating contains the microscopic particles of inorganic substance, the content of these particles per unit weight of the ink or coating is preferably in a range of 5% by weight to 40% by weight. When the ink or the coating contains the hydrophilically modifying agent, the content of the hydrophilically modifying agent per unit weight of the ink or coating is preferably in a range of 0.5% by weight to 5.0% by weight. When the ink or coating contains the hydrophilic acrylic binder, the content of the hydrophilically modifying agent per unit weight of the ink or coating is preferably in a range of 5% by weight to 25% by weight.

The composite nonwoven fabric 31A exhibits a Klemm's water absorbency in a range of 1 mm to 90 mm. If the Klemm's water absorbency of the composite nonwoven fabric 31A is less than 1 mm, diffusibility as well as absorbability for body fluids in the nonwoven fabric 31A will be insufficient to ensure that the nonwoven fabric 31A can rapidly absorb urine and thereby the display elements 33 can become visible immediately after urine has been discharged. The Klemm's water absorbency of the composite nonwoven fabric 31A was measured by a method as follows:

(1) Samples of the same nonwoven fabric as the composite nonwoven fabric 31A (each dimensioned to be 150 mm×25 mm) were prepared as Klemm's water absorbency measurement samples. For measurement of the Klemm's water absorbency, a laboratory dish filled with water, a stand provided with a vertical shaft and an arm horizontally extending from the top of the shaft, and a ruler were used.

(2) The laboratory dish was placed below the arm of the stand, one of longitudinally opposite ends of the sample was attached to the distal end of the arm of the stand so that the sample may hang down from the arm, and the other end of the sample was immersed in the water filling the laboratory dish for 10 minutes. After 10 minutes have elapsed, a height by which the sample had absorbed the water (i.e., a height from the surface of the water) was measured using the ruler and the value measured in this manner was employed as the Klemm's water absorbency. The height by which the sample had absorbed was in a range of 1 mm to 90 mm.

The composite nonwoven fabric 31A has a water absorbency per unit weight in a range of 5% by weight to 600% by weight. If the water absorbency per unit weight of the composite nonwoven fabric 31A is less than 5% by weight, the nonwoven fabric 31A will be insufficiently wetted with urine to achieve a sufficient reduction of the luminous diffusive reflection on the nonwoven fabric 31A even after the nonwoven fabric 31A has absorbed urine. Consequentially, it may be impossible to make the display elements 33 clearly visible after urine has been discharged. The water absorbency per unit weight of the composite nonwoven fabric 31A was measured by a method as follows:

(1) Samples of the same nonwoven fabric as the composite nonwoven fabric 31A (each dimensioned to be 150 mm×25 mm) were prepared as the water absorbency measurement samples. For measurement of the water absorbency, a beaker filled with water and a weightometer were used.

(2) Weight A of the sample in its dry state was measured by the weightometer. Then the sample was completely immersed in water and left for 1 minute. After 1 minute has elapsed, the sample was taken out from the beaker and left 30 seconds in air. Weight B of the sample having absorbed water was measured by the weightometer. Water absorbency was calculated according to $\{(B-A)/A\}\times 100$ and a value calculated in this manner was employed as the water absorbency. The water absorbency of this sample was in a range of 5% by weight to 600% by weight.

An area ratio of the heat-embossed spots 34 to unit area of the composite nonwoven fabric 31A is in a range of 5% to 50%. If the area ratio is less than 5%, it will be impossible to utilize the heat-embossed spots 34 for the purpose of making the display elements 33 clearly visible. If the area ratio exceeds 50%, the brightness as well as the color saturation of the display elements 33 will not sufficiently change between in the dry state and in the wetted state of the nonwoven fabric 31A to ensure that the indicator 19A can clearly indicate whether urine has been discharged or not.

Figure 2:
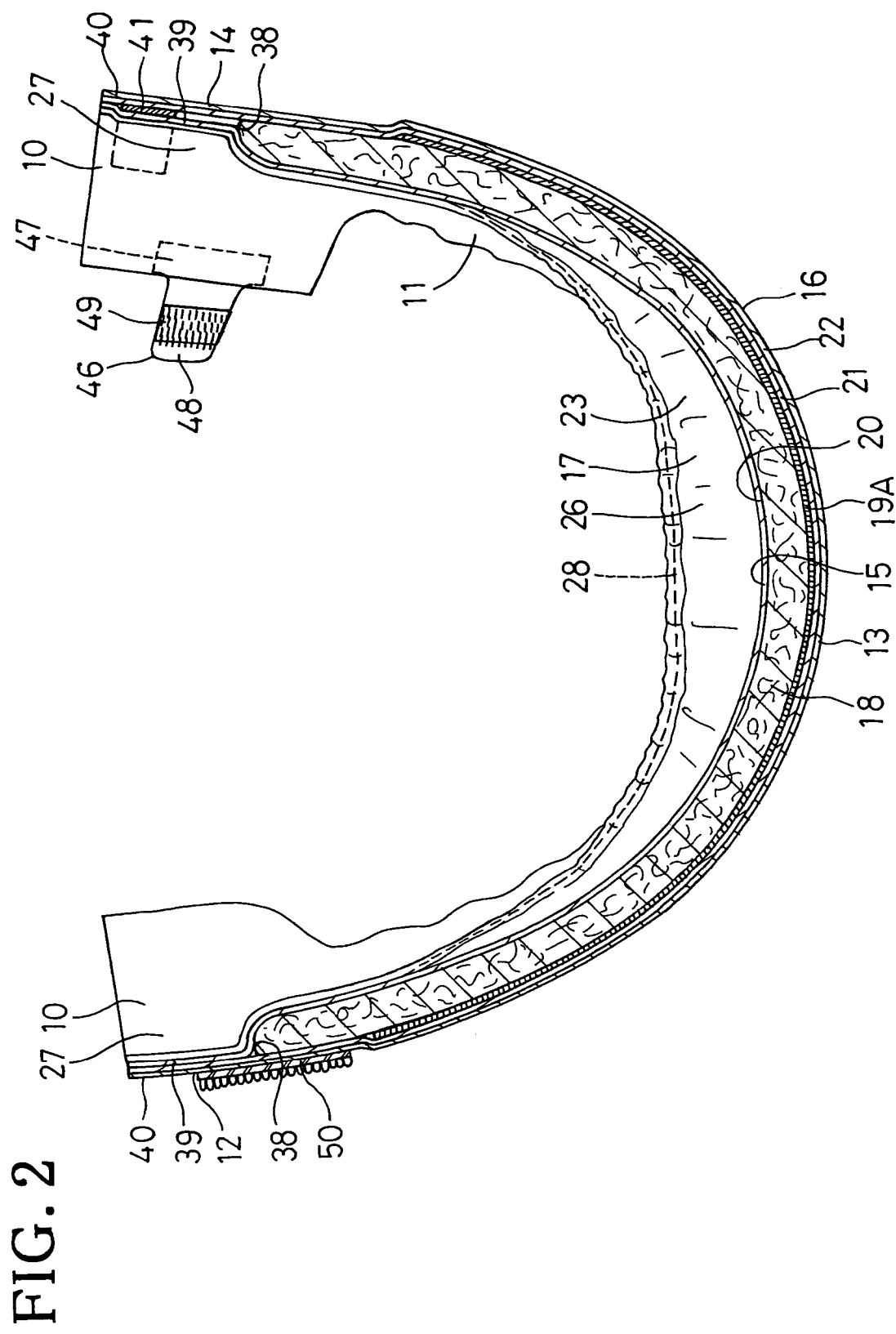
FIG. 2 is a sectional view taken along the line 2-2 in FIG. 1.
Figure 3:
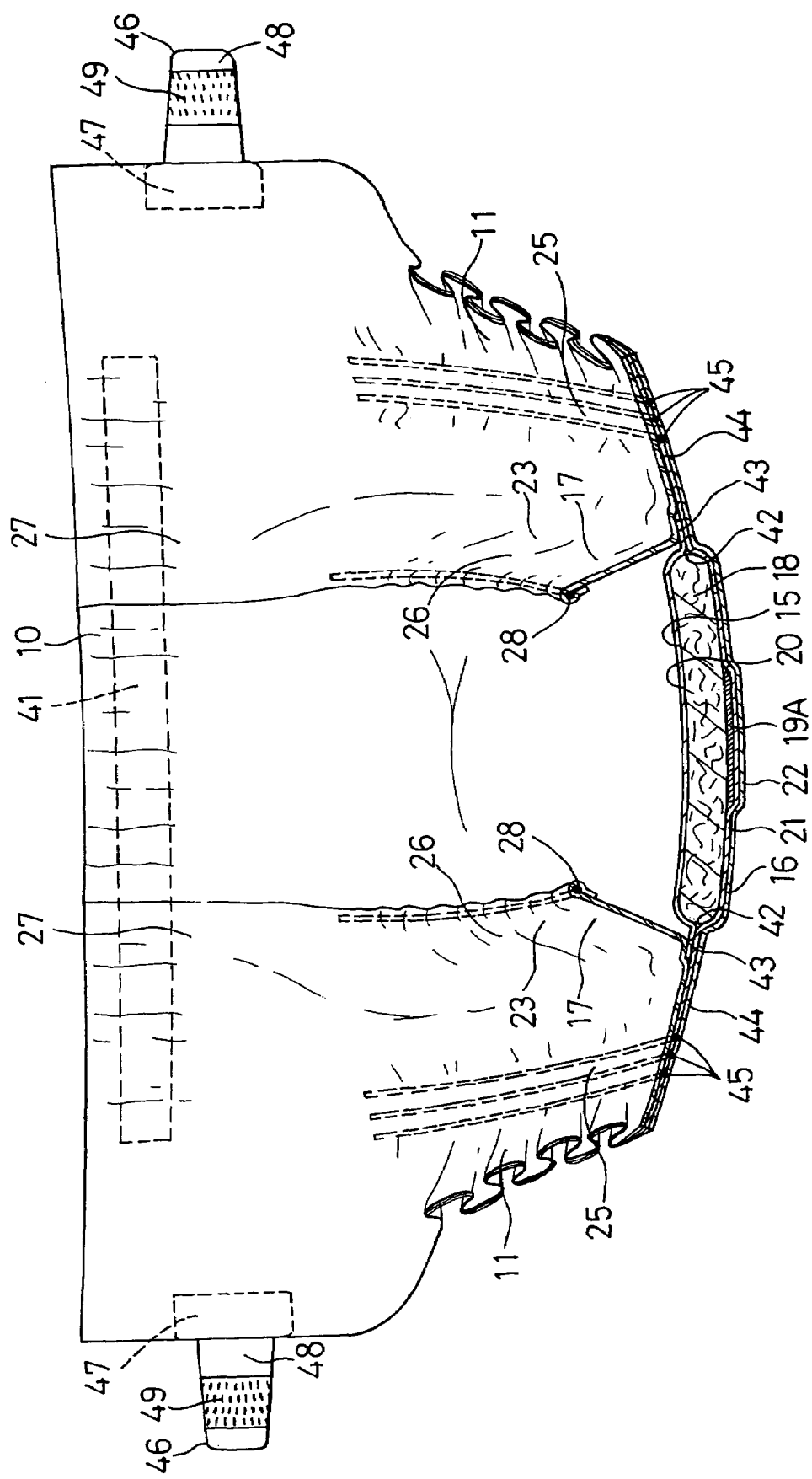
FIG. 3 a sectional view taken along the line 3-3 in FIG. 1.
Figure 4:
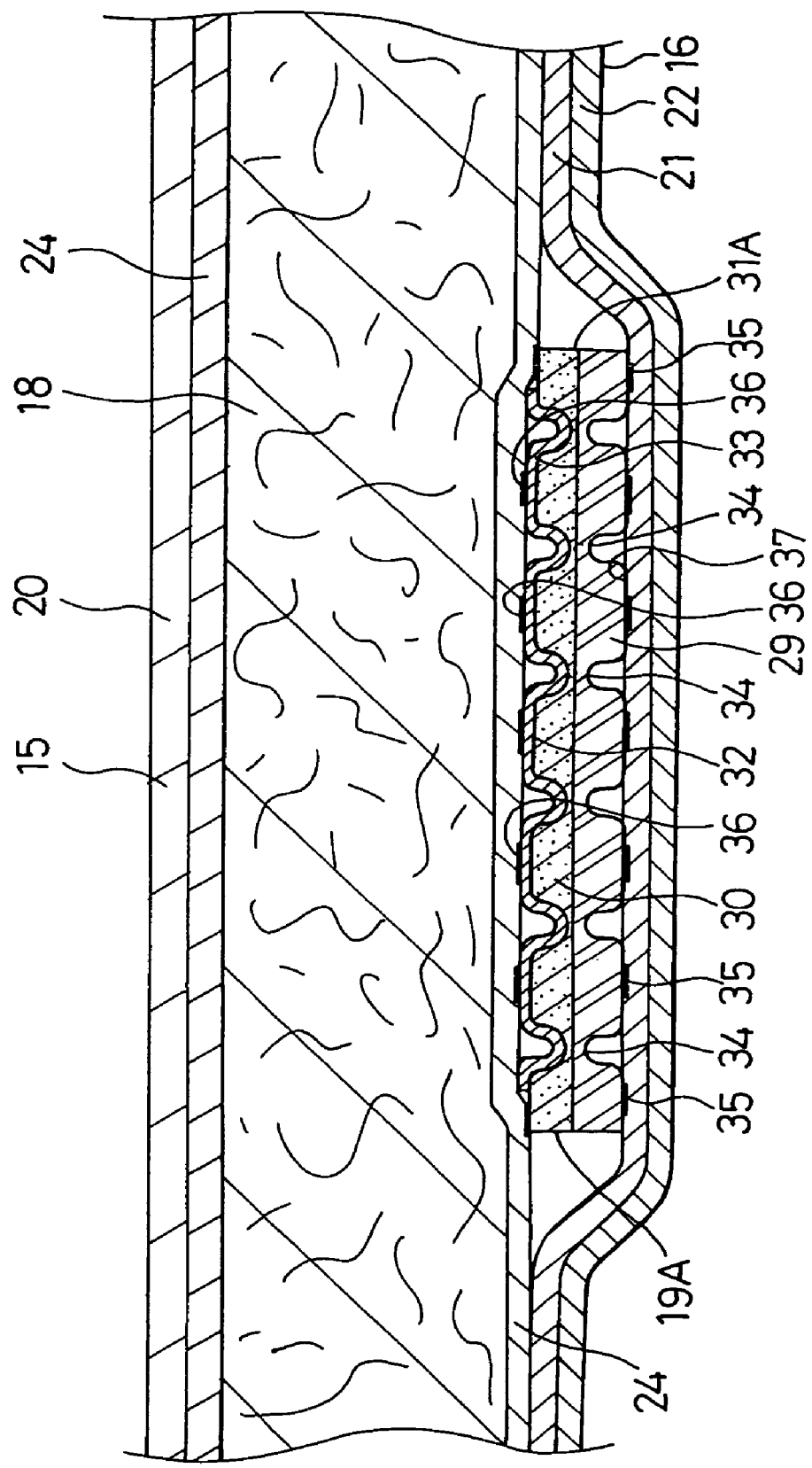
FIG. 4 is a scale-enlarged sectional view taken along the line 4-4 in FIG. 1.
Figure 6:
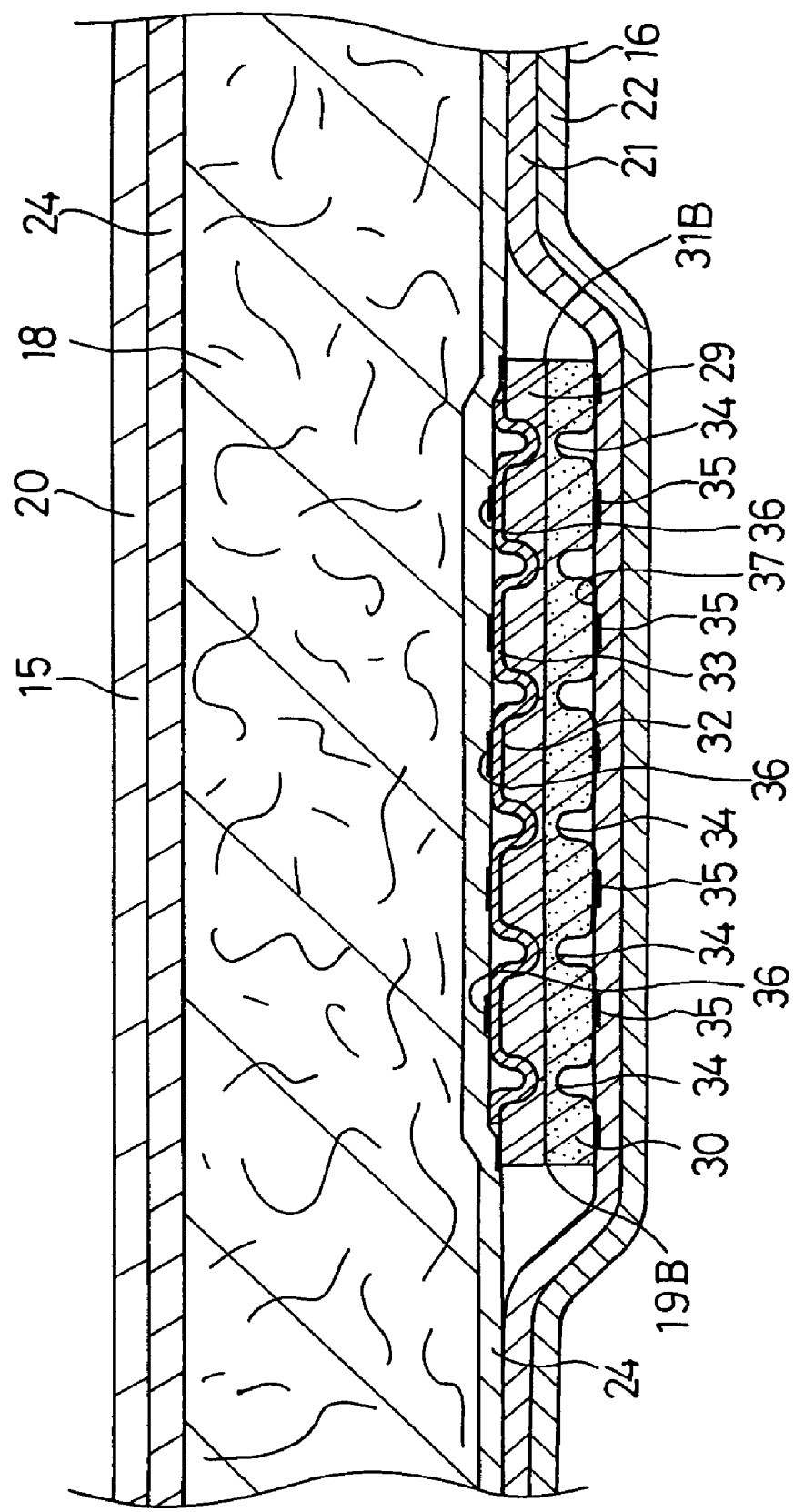
FIG. 6 is a view similar to FIG. 4, showing a preferred second embodiment of this invention.

Referring to FIG. 6 showing an indicator 19B according to a second embodiment of this invention, the features of the diaper except the indicator 19B have previously been described with reference to FIGS. 1 through 3 in the first embodiment and will not be repetitively described hereinafter but merely those FIGS. 1 through 3 will be quoted if desired.

The indicator 19B is similar to the indicator 19A in the first embodiment except the indicator 19B includes a composite nonwoven fabric 31B in place of the composite nonwoven fabric 31A.

The composite nonwoven fabric 31B is composed of a hydrophilic melt blown nonwoven fabric layer 29 and a hydrophilic spun bond nonwoven fabric layer 30 laminated on one surface of the melt blown nonwoven fabric 29 similarly to the composite nonwoven fabric 31A in the first embodiment. In the second embodiment, the spun bond nonwoven fabric layer 30 faces the backsheet 16 and the melt blown nonwoven fabric layer 29 faces the core 18, unlike in the first embodiment. The basis weight as well as the fiber density of the melt blown nonwoven fabric layer 29 and the spun bond nonwoven fabric layer 30 are the same as those of the nonwoven fabric layers 29, 30 in the first embodiment. The composite nonwoven fabric 31B contains a predetermined amount of hydrophilically modifying agent. The display elements 33 are images of bear's face arranged at predetermined intervals in the longitudinal direction and depicted on the melt blown nonwoven fabric layer 29 so that each of these images may occupy a part of the heat-embossed spot 34 as well as a part of the region surrounding the heat-embossed spot 34.

Urine discharged on the diaper put on the wearer's body is absorbed by the core 18 through the topsheet 15, then transferred from the core 18 to the composite nonwoven fabric 31B defining the indicator 19B and absorbed thereby. Before urine is discharged on the diaper, the indicator 19B is in its dry state and the display elements 33 are covered up by the composite nonwoven fabric 31B. The display elements 33 are covered up by the melt blown nonwoven fabric layer 29 having a high cover-up effect and the outlines of the display elements 33 can be vaguely recognized but the display elements 33 in entirety can not be clearly recognized.

Urine having been discharged on the diaper is transferred from the core 18 to the melt blown nonwoven fabric layer 29, then rapidly absorbed by the melt blown nonwoven fabric layer 29 and, at the same time, transferred from the melt blown nonwoven fabric layer 29 to the spun bond nonwoven fabric layer 30 so that urine rapidly spreads in the spun bond nonwoven fabric 30 and is absorbed by this nonwoven fabric layer 30. In the diaper, the melt blown nonwoven fabric layer 29 and the spun bond nonwoven fabric layer 30 rapidly absorb urine under the effect of capillary action and thereupon the luminous diffusion in these nonwoven fabric layers 29, 30 is rapidly reduced. Consequentially, the display elements 33 become visible immediately because the luminous transmittance of the nonwoven fabric 31B is correspondingly enhanced and brightness as well as color saturation of the display elements 33 is also enhanced as viewed from the outside of the backsheet 16. In this way, the display elements 33 in entirety can be clearly recognized from the outside of the backsheet 16 as urine is discharged thereon. The display elements 33 become visible as soon as urine is discharged on the diaper, so that the indicator 19B allows the parent or the care personnel to perceive occurrence of urination from the outside of the backsheet 16 immediately after it has occurred. The backsheet 16 also is wetted with urine as the composite nonwoven fabric 31B is wetted with urine. In other words, the luminous transmittance of the backsheet 16 is enhanced and ensures that the display elements 33 having become visible in entirety thereof can be reliably recognized from the outside of the backsheet 16.

The total luminous transmittances of the composite nonwoven fabric 31B in its dry and wetted states are the same as those exhibited by the nonwoven fabric 31A in the first embodiment and the contents of the hydrophilically modifying agent per unit weight in the composite nonwoven fabric 31B are also the same as those in the nonwoven fabric 31A in the first embodiment. The Klemm's water absorbency exhibited by the composite nonwoven fabric 31B is the same as in the nonwoven fabric 31A in the first embodiment and the water absorbency per unit weight exhibited by the composite nonwoven fabric 31B also is the same as in the nonwoven fabric 31A in the first embodiment. The area ratio of the heat-embossed spots 34 to unit area of the composite nonwoven fabric 31B is the same as in the nonwoven fabric 31A in the first embodiment. Methods for measurement of the total luminous transmittance, the Klemm's water absorbency and water absorbency exhibited by the composite nonwoven fabric 31B are the same as those used for the nonwoven fabric 31A in the first embodiment.

Figure 7:
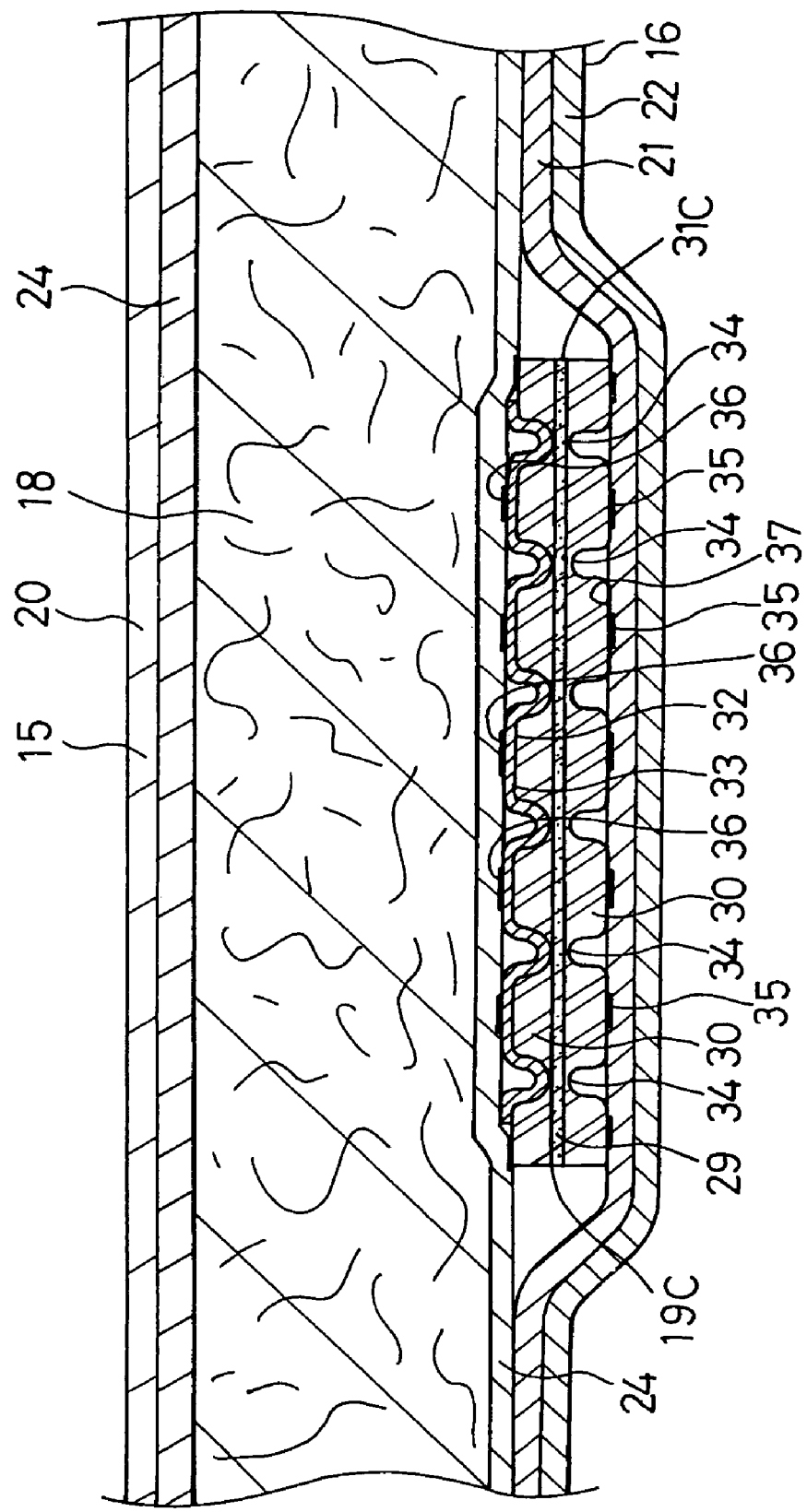
FIG. 7 is a view similar to FIG. 4, showing a preferred third embodiment of this invention.

Referring to FIG. 7 showing an indicator 19C according to a third embodiment of this invention, the features of the diaper except the indicator 19C have previously been described with reference to FIGS. 1 through 3 in the first embodiment and will not be repetitively described hereinafter but merely those FIGS. 1 through 3 will be quoted if desired.

The indicator 19C is similar to the indicator 19A in the first embodiment except including a composite nonwoven fabric 31C in place of the composite nonwoven fabric 31A in the first embodiment. The composite nonwoven fabric 31C is composed of a hydrophilic melt blown nonwoven fabric layer 29 and a spun bond nonwoven fabric layer 29 and the spun bond nonwoven fabric layers 30 face the backsheet 16 and the core 18, respectively, and the melt blown nonwoven fabric layer 29 is sandwiched between the spun bond nonwoven fabric layers 30. The composite nonwoven fabric 31C is formed with a plurality of heat-embossed spots 34 which are depressed in its thickness direction. At these heat-embossed spots 34, the composite nonwoven fabric 31C are compressed under heating in its thickness direction so that the composite nonwoven fabric 31C may present a substantially film-like state and the melt blown nonwoven fabric layer 29 may be integrated with the spun bond nonwoven fabric layers 30. The spun bond nonwoven fabric layers 30 are bonded to the backsheet 16 and the core 18 by means of adhesives 35, 36 intermittently applied to the spun bond nonwoven layers 29 and held in close contact with the backsheet 16 and the core 18. The composite nonwoven fabric 31C has its first surface 32 held together with the display elements 33 in close contact with the surface of the core 18 and its second surface 37 facing the backsheet 16 held in close contact with the inner surface of the backsheet 16.

To form the composite nonwoven fabric 31C, the spun bond nonwoven fabric layer 30 is made, the melt blown nonwoven fabric layer 29 is accumulated, while this layer 29 is made, on one surface of the spun bond nonwoven fabric layer 30 traveling on the net conveyor and then another spun bond nonwoven fabric layer 30 is accumulated on the melt blown nonwoven fabric layer 29. The component fibers of these nonwoven fabric layers 29, 30, respectively, intersect with one another and are fused together at the points of intersection. The component fibers of these nonwoven fabric layers 29, 30 may be the same as those used for the nonwoven fabric layers 20, 22, 23. The method to forming the composite nonwoven fabric 31C with the heat-embossed spots 34 is the same as the method used for the composite nonwoven fabric 31A in the first embodiment. As for the basis weight and the fiber density also, the melt blown nonwoven fabric layer 29 and the spun bond nonwoven fabric layer 30 of the composite nonwoven fabric 31C are similar to those of the composite nonwoven fabric 31A in the first embodiment. The composite nonwoven fabric 31C has a basis weight in a range of 9 g/m$^2$ to 210 g/m$^2$ and a fiber density in a range of 0.012 g/cm$^3$ to 0.3 g/cm$^3$. The composite nonwoven fabric 31C contains a predetermined amount of hydrophilically modifying agent.

Urine discharged on the diaper put on the wearer's body is absorbed by the core 18 through the topsheet 15 and then absorbed from the core 18 by the composite nonwoven fabric 31C defining the indicator 19C. Before urine is discharged on the diaper, the indicator 19C is in its dry state and the display elements 33 are covered up by the composite nonwoven fabric 31C. The display elements 33 are covered up by the melt blown nonwoven fabric layer 29 having a high cover-up effect and the outlines of the display elements 33 can be vaguely recognized but the display elements 33 in entirety can not be clearly recognized as viewed from the outside of the backsheet 16.

Urine having been discharged on the diaper transfers from the core 18 to the spun bond nonwoven fabric layer 30 and rapidly spreads in the spun bond nonwoven fabric layer 30 in its entirety. At the same time, the melt blown nonwoven fabric layer 29 and the spun bond nonwoven fabric layer 30 rapidly absorb urine under the effect of capillary action and the light scattering in these nonwoven fabric layers 29, 30 is rapidly reduced. Consequentially, the display elements 33 become visible immediately since the luminous transmittance of the nonwoven fabric 31C is correspondingly enhanced and brightness as well as color saturation of the display elements 33 is also enhanced as viewed from the outside of the backsheet 16. In this way, the display elements 33 in entirety can be clearly recognized from the outside of the backsheet 16. The display elements 33 become visible as soon as urine is discharged on the diaper, so that the indicator 19C allows the parent or the care personnel to perceive occurrence of urination from the outside of the backsheet 16 immediately after it has occurred. In this diaper, the backsheet 16 also is wetted with urine as the composite nonwoven fabric 31C is wetted with urine. In other words, the luminous transmittance of the backsheet 16 is enhanced and ensures that the display elements 33 having become visible in entirety thereof can be reliably recognized from the outside of the backsheet 16.

With respect to the total luminous transmittance in a dry state and in a wetted state, the content of the hydrophilically modifying agent per unit weight, the Klemm's water absorbency, the water absorbency per unit weight and the area ratio of the heat-embossed spots 34 per unit area, the composite nonwoven fabric 31C is similar to the composite nonwoven fabric 31A in the first embodiment. The methods to measure the total luminous transmittance, the content of the hydrophilically modifying agent, the Klemm's water absorbency and the water absorbency of the composite nonwoven fabric 31C are the same as those used for the composite nonwoven fabric 31A in the first embodiment.

Figure 8:
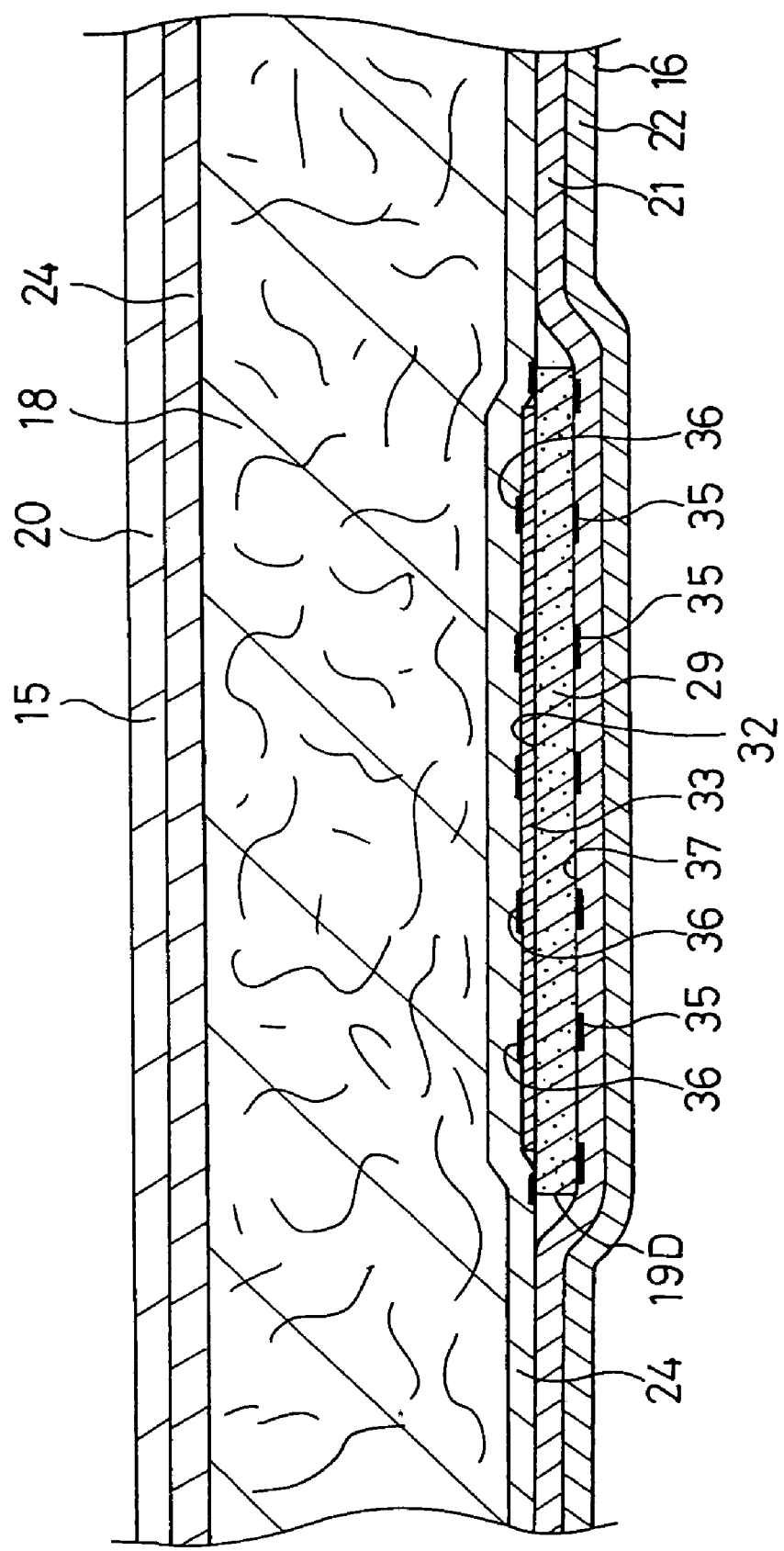
FIG. 8 is a view similar to FIG. 4, showing a preferred fourth embodiment of this invention.

Referring to FIG. 8 showing an indicator 19D according to a fourth embodiment of this invention, the features of the diaper except the indicator 19D have previously been described with reference to FIGS. 1 through 3 in the first embodiment and will not be repetitively described hereinafter but merely those FIGS. 1 through 3 will be quoted if desired.

The indicator 19D is similar to the indicator 19A in the first embodiment except that the indicator 19D is composed of the hydrophilic melt blown nonwoven fabric layer 29 and the display elements 33 depicted on a first surface 32 of the melt blown nonwoven fabric layer 29 facing the core 18 and that the nonwoven fabric layer 29 is formed with none of the heat-embossed spots 34.

The melt blown nonwoven fabric layer 29 is bonded to the backsheet 16 and to the core 18 by means of adhesives 35, 36, respectively, intermittently applied on the nonwoven fabric layer 29. The nonwoven fabric layer 29 has its first surface 32 held together with the display elements 33 in close contact with the surface of the core 18 and its second surface 37 facing the backsheet 16 held in close contact with the inner surface of the backsheet 16. The basis weight and the fiber density of the melt blown nonwoven fabric layer 29 are same as those of the nonwoven fabric layer 29 in the first embodiment. The nonwoven fabric layer 29 contains a predetermined amount of hydrophilically modifying agent.

Urine discharged on the diaper put on the wearer's body is absorbed by the core 18 through the topsheet 15 and then absorbed from the core 18 by the melt blown nonwoven fabric layer 29 defining the indicator 19D. Before urine is discharged on the diaper, the indicator 19D is in its dry state and the display elements 33 are covered up by the melt blown nonwoven fabric layer 29. The display elements 33 are covered up by the melt blown nonwoven fabric layer 29 having a high cover-up effect and the outlines of the display elements 33 can be vaguely recognized but the display elements 33 in entirety can not be clearly recognized as viewed from the outside of the backsheet 16.

Urine having been discharged on the diaper transfers from the core 18 to the melt blown nonwoven fabric layer 29 and the melt blown nonwoven fabric layer 29 rapidly absorb urine under the effect of capillary action and the light scattering in this nonwoven fabric layers 29 is rapidly reduced and the display elements 33 become visible immediately at once. Reduction of the light scattering in the nonwoven fabric layer 29 correspondingly enhances the luminous transmittance of the nonwoven fabric layer 29. Consequentially, the luminous brightness as well as color saturation of the display elements 33 is also enhanced as viewed from the outside of the backsheet 16. In this way, the display elements 33 as a whole can be clearly recognized from the outside of the backsheet 16. The display elements 33 become visible as soon as urine is discharged on the diaper, so that the indicator 19D allows the parent or the care personnel to perceive occurrence of urination from the outside of the backsheet 16 immediately after it has occurred. The backsheet 16 also is wetted with urine as the melt blown nonwoven fabric layer 29 is wetted with urine. In other words, the luminous transmittance of the backsheet 16 is enhanced and ensures that the display elements 33 having become visible in entirety thereof can be reliably recognized from the outside of the backsheet 16.

The melt blown nonwoven fabric layer 29 exhibits a total luminous transmittance in a range of 20% to 40% in its dry state and in a range of 60% to 95% in its wetted state. If the total luminous transmittance of the melt blown nonwoven fabric layer 29 in its dry state exceeds 40%, the nonwoven fabric layer 29 will no more have a desired cover-up effect for the display elements 33 and the brightness as well as the color saturation of the display elements 33 as viewed from the outside of the backsheet 16 will not sufficiently change between in the dry state and in the wetted state of the nonwoven fabric layer 29 to ensure that the indicator 19D can clearly indicate whether urine has been discharged or not. If the total luminous transmittance of the melt blown nonwoven fabric layer 29 in its wetted state is less than 60%, the nonwoven fabric layer 29 will maintain a relatively high cover-up effect for the display elements 33 even after the nonwoven fabric layer 29 has absorbed urine and it may be impossible for the parent or the care personnel to see the display elements 33 clearly through the nonwoven fabric layer 29 from the outside of the backsheet 16 and to perceive that urine has been discharged. The total luminous transmittance of the melt blown nonwoven fabric layer 29 in its dry state and in its wetted state was measured by the same method as used for the nonwoven fabric layer 29 in the first embodiment.

A content of hydrophilically modifying agent per unit weight, a Klemm's water absorbency and water absorption per unit weight of the melt blown nonwoven fabric layer 29 are the same as in the case of the composite nonwoven fabric 31A in the first embodiment. The methods for measurement of Klemm's water absorbency and water absorption exhibited by the melt blown nonwoven fabric layer 29 are also the same as used for the nonwoven fabric 31A in the first embodiment.

Figure 9:
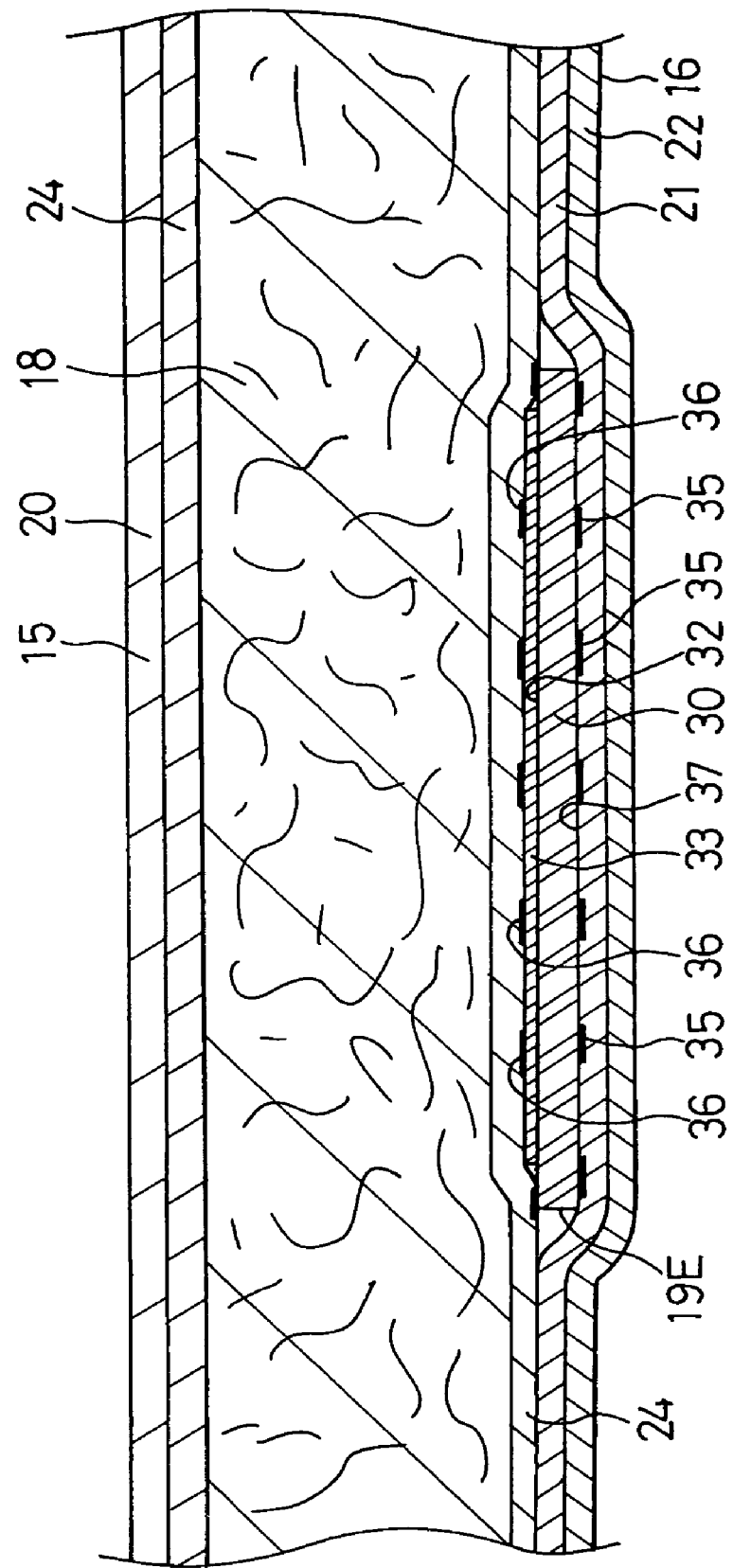
FIG. 9 is a view similar to FIG. 4, showing a preferred fifth embodiment of this invention.

Referring to FIG. 9 showing an indicator 19E according to a fifth embodiment of this invention, the features of the diaper except the indicator 19E have previously been described with reference to FIGS. 1 through 3 in the first embodiment and will not be repetitively described hereinafter but merely those FIGS. 1 through 3 will be quoted if desired.

The indicator 19E is similar to the indicator 19A in the first embodiment except that the indicator 19E is the hydrophilic spun bond nonwoven fabric 30 and display elements 33 depicted on a first surface 32 of the spun bond nonwoven fabric layer 30 facing the core 18 and the nonwoven fabric layer 30 is formed with none of the heat-embossed spots 34.

The spun bond nonwoven fabric layer 30 is bonded to the backsheet 16 and to the core 18 by means of adhesives 35, 36, respectively, intermittently applied on the nonwoven fabric layer 30. The nonwoven fabric layer 30 has its first surface 32 held together with the display elements 33 in close contact with the surface of the core 18 and its second surface 37 facing the backsheet 16 held in close contact with the inner surface of the backsheet 16. The basis weight and the fiber density of the spun bond nonwoven fabric layer 30 are the same as those of the nonwoven fabric layer 30 in the first embodiment. The spun bond nonwoven fabric layer 30 contains a predetermined amount of hydrophilically modifying agent.

Urine discharged on the diaper put on the wearer's body is absorbed by the core 18 through the topsheet 15 and then absorbed from the core 18 by the spun bond nonwoven fabric layer 30 defining the indicator 19E. Before urine is discharged on the diaper, the indicator 19E is in its dry state and the display elements 33 are covered up by the spun bond nonwoven fabric layer 30. In the diaper, the display elements 33 are covered up by the spun bond nonwoven fabric layer 30 having a high cover-up effect and the outlines of the display elements 33 can be vaguely recognized but the display elements 33 in entirety can not be clearly recognized as viewed from the outside of the backsheet 16.

Urine having been discharged on the diaper transfers from the core 18 to the spun bond nonwoven fabric layer 30 and rapidly spreads in the spun bond nonwoven fabric layer 30 in its entirety. At the same time, the nonwoven fabric layer 30 rapidly absorbs urine under the effect of capillary action and the luminous diffusion in these nonwoven fabric layers 30 is rapidly reduced. Consequentially, the display elements 33 become visible immediately since the luminous transmittance of the nonwoven fabric layer 30 is correspondingly enhanced and brightness as well as color saturation of the display elements 33 is also enhanced as viewed from the outside of the backsheet 16. In this way, the display elements 33 in entirety can be clearly recognized from the outside of the backsheet 16. The display elements 33 become visible as soon as urine is discharged on the diaper, so that the indicator 19E allows the parent or the care personnel to perceive occurrence of urination from the outside of the backsheet 16 immediately after it has occurred. In this diaper, the backsheet 16 also is wetted with urine as the spun bond nonwoven fabric layer 30 is wetted with urine. In other words, the luminous transmittance of the backsheet 16 is enhanced and ensures that the display elements 33 having become visible in entirety thereof can be reliably recognized from the outside of the backsheet 16.

The spun bond nonwoven fabric layer 30 exhibits a total luminous transmittance in a range of 20% to 40% in its dry state and in a range of 60% to 95% in its wetted state. If the total luminous transmittance of the spun bond nonwoven fabric layer 29 in its dry state exceeds 40%, the nonwoven fabric layer 30 will no more have a desired cover-up effect for the display elements 33 and the brightness as well as the color saturation of the display elements 33 as viewed from the outside of the backsheet 16 will not sufficiently change between in the dry state and in the wetted state of the nonwoven fabric layer 30 to ensure that the indicator 19E can clearly indicate whether urine has been discharged or not. If the total luminous transmittance of the spun bond nonwoven fabric layer 30 in its wetted state is less than 60%, the nonwoven fabric layer 30 will maintain a relatively high cover-up effect for the display elements 33 even after the nonwoven fabric layer 30 has absorbed urine and it may be impossible for the parent or the care personnel to see the display elements 33 clearly through the nonwoven fabric layer 30 from the outside of the backsheet 16 and to perceive that urine has been discharged. The total luminous transmittance of the spun bond nonwoven fabric layer 30 in its dry state and in its wetted state was measured by the same method as used for the nonwoven fabric layer 30 in the first embodiment.

A content of hydrophilically modifying agent per unit weight, a Klemm's water absorbency and water absorption per unit weight of the melt blown nonwoven fabric layer 30 are the same as in the case of the composite nonwoven fabric 31A in the first embodiment.

In operative association with the indicators 19A, 19B and 19C in the first, second and third embodiments, respectively, it is not essential to form the composite nonwoven fabric 31A, 31B, 31C with the heat-embossed spots 34. In operative association with the indicators 19D, 19E in the fourth and fifth embodiments, the nonwoven fabric layers 29, 30 may be formed with the heat-embossed spots 34. The display elements 33 depicted on the indicators 19A, 19B, 19C, 19D, 19E are not limited to bears' faces and the other graphics, symbols and patterns may be depicted in the place of bears' faces. The indicators 19A, 19B, 19C, 19D, 19E may extend in the longitudinal direction over the crotch region 13 and further into one of the front and rear waist regions 12, 14 or may be laid in at least one of the front and rear waist regions 12, 14 and extend in the transverse direction over the longitudinal midsection of the front or rear waist region 12, 14.

Material for the topsheet 15 may be selected from the group consisting of a hydrophilic fibrous nonwoven fabric, hydrophobic fibrous nonwoven fabric having a plurality of perforations and plastic film having a plurality of fine perforations. It is also possible to form the backsheet 16 from a composite nonwoven fabric comprising two or more hydrophobic fibrous nonwoven fabric layers laminated together. Similarly to the indicators, it is possible to form the backsheet 16 and the leak-barrier cuffs 17 using the composite nonwoven fabric consisting of the melt blown nonwoven fabric layer and one or two spun bond nonwoven fabric layer(s) laminated on one or both surface(s) of the melt blown nonwoven fabric layer.

Bonding of the top- and backsheets 15, 16 to each other, permanently bonding of the top- and backsheets 15, 16 and the leak-barrier cuffs 17 one to another, bonding of the core 18 to the sheets 15, 16 and bonding of the elastic members 28, 41, 45 to the sheets 15, 16 and the cuffs 17, respectively, may be carried out using adhesive or welding means such as heat-sealing or sonic sealing. The adhesives may be selected from the group consisting of hot melt adhesives, acrylic adhesives and rubber adhesives.

The adhesives are preferably applied on the topsheet 15, the backsheet 16 and the leak-barrier cuffs 17 in a pattern selected from a spiral pattern, wave pattern, zigzag pattern, dotted pattern and striped pattern. The adhesives may be applied on the sheets 15, 16 and the cuffs 17 in these patterns to define adhesive zones and non-adhesive zones in these sheets 15, 16 and the cuffs 17. Consequentially, these sheets 15, 16 and the cuffs 17 are intermittently bonded one to another, the core 18 is intermittently bonded to these sheets 15, 16, and the elastic members 28, 41, 45 are intermittently bonded to the sheets 15, 16 and the cuffs 17.

The entire discloses of Japanese Patent Application No. 2004-220165 filed on Jul. 28, 2004 including specification, drawings and abstract are herein incorporated by reference in its entirety.

What is claimed is:

1. An absorbent article, comprising:
a liquid-pervious topsheet;
a light transmissive and liquid-impervious backsheet;
a liquid-absorbent core interposed between said topsheet and said backsheet;
an indicator disposed between said backsheet and said core for allowing discharge of bodily fluids to be visible from an outside of said backsheet when said indicator is wetted with bodily fluids; and
said indicator comprising a hydrophilic fibrous nonwoven fabric and a display element depicted on said hydrophilic fibrous nonwoven fabric so that said hydrophilic fibrous nonwoven fabric covers up said display element so long as said hydrophilic fibrous nonwoven fabric is in a dry state and allows said display element to be visible though said hydrophilic fibrous nonwoven fabric from the outside of said backsheet when said hydrophilic fibrous nonwoven fabric absorbs bodily fluids;
wherein said hydrophilic fibrous nonwoven fabric comprises at least one of a hydrophilic melt blown nonwoven fabric layer and a hydrophilic spun bond nonwoven fabric layer, said display element being depicted on a first surface of said hydrophilic fibrous nonwoven fabric facing said core, said first surface of said hydrophilic fibrous nonwoven fabric being held together with said display element in close contact with the surface of said core, and a second surface of said hydrophilic fibrous nonwoven fabric facing said backsheet being held in close contact with an inner surface of said backsheet;
wherein the hydrophilic fibrous nonwoven fabric comprises depressions on both first and second surfaces thereof, said depressions being heat-embossed spots that are depressed, in a thickness direction of the hydrophilic fibrous nonwoven fabric, from one of the first and second surfaces toward the other.

2. The absorbent article as defined by claim 1, wherein said hydrophilic fibrous nonwoven fabric comprises a hydrophilic melt blown nonwoven fabric layer and a hydrophilic spun bond nonwoven fabric layer laminated together.

3. The absorbent article as defined by claim 1, wherein said hydrophilic fibrous nonwoven fabric contains a hydrophilically modifying agent per unit weight in a range of 0.5% by weight to 5.0% by weight.

4. The absorbent article as defined by claim 1, wherein said hydrophilic fibrous nonwoven fabric exhibits a Klemm's water absorbency in a range of 1 mm to 90 mm.

5. The absorbent article as defined by claim 4, wherein said hydrophilic fibrous nonwoven fabric exhibits a total luminous transmittance in a range of 20% to 40% in its dry state and in a range of 60% to 95% when said hydrophilic fibrous nonwoven fabric absorbs bodily fluids.

6. The absorbent article as defined by claim 1, wherein said hydrophilic fibrous nonwoven fabric exhibits a water absorbency per unit weight in a range of 5% by weight to 600% by weight.

7. The absorbent article as defined by claim 1, wherein the thickness of the hydrophilic fibrous nonwoven fabric at the heat-embossed spots is smaller than in other parts of the hydrophilic fibrous nonwoven fabric surrounding said heat-embossed spots.

8. The absorbent article as defined by claim 7, wherein said hydrophilic fibrous nonwoven fabric has said heat-embossed spots at an area ratio to unit area of said hydrophilic fibrous nonwoven fabric in a range of 5% to 50% and said display element occupies a part of said heat-embossed spots as well as a part of a region surrounding said heat-embossed spots.

9. The absorbent article as defined by claim 8, wherein said display element is formed on said hydrophilic fibrous nonwoven fabric with one of an ink layer and a coating layer.

10. The absorbent article as defined by claim 7, wherein the heat-embossed spots depressed from the first surface of the hydrophilic fibrous nonwoven fabric corresponds in position to the heat-embossed spots depressed from the second surface of the hydrophilic fibrous nonwoven fabric.

11. The absorbent article as defined by claim 7, wherein said hydrophilic fibrous nonwoven fabric is not directly bonded to said core or said back sheet at said heat-embossed spots.

12. The absorbent article as defined by claim 11, wherein said hydrophilic fibrous nonwoven fabric has a state of a film in said heat-embossed spots.

13. The absorbent article as defined by claim 7, the first and second surfaces of said hydrophilic fibrous nonwoven fabric comprising regions that surround said heat-embossed spots and are bonded by adhesive to the core and the backsheet, respectively.

14. The absorbent article as defined by claim 13, wherein said display element comprises an ink layer or a coating layer directly printed or coated, respectively, on the first surface of the hydrophilic fibrous nonwoven fabric both in the heat-embossed spots and in the regions that surround said heat-embossed spots.

15. The absorbent article as defined by claim 14, wherein said ink or coating is in direct contact with the core in the regions that surround said heat-embossed spots.

16. The absorbent article as defined by claim 14, wherein said hydrophilic fibrous nonwoven fabric exhibits a Klemm's water absorbency in a range of 1 mm to 90 mm.

17. The absorbent article as defined by claim 16, wherein said hydrophilic fibrous nonwoven fabric exhibits a total luminous transmittance in a range of 20% to 40% in its dry state and in a range of 60% to 95% when said hydrophilic fibrous nonwoven fabric absorbs bodily fluids.

18. The absorbent article as defined by claim 1, wherein
said hydrophilic fibrous nonwoven fabric comprises said hydrophilic melt blown nonwoven fabric layer and two said hydrophilic spun bond nonwoven fabric layers;
said first surface of said hydrophilic fibrous nonwoven fabric is defined by one of the hydrophilic spun bond nonwoven fabric layers, and held together with said display element in close contact with the surface of said core;
said second surface of said hydrophilic fibrous nonwoven fabric facing said backsheet is defined by the other of the hydrophilic spun bond nonwoven fabric layers and held in close contact with an inner surface of said backsheet; and
said hydrophilic melt blown nonwoven fabric layer is sandwiched between said two hydrophilic spun bond nonwoven fabric layers and is integrated with both said two hydrophilic spun bond nonwoven fabric layers in said heat-embossed spots.

19. The absorbent article as defined by claim 1, wherein
said hydrophilic fibrous nonwoven fabric comprises said hydrophilic melt blown nonwoven fabric layer; and
the display element is depicted on the hydrophilic melt blown nonwoven fabric layer facing the absorbent core.

20. The absorbent article as defined by claim 1, wherein
said hydrophilic fibrous nonwoven fabric comprises said hydrophilic spun bond nonwoven fabric layer; and
the display element is depicted on the hydrophilic spun bond nonwoven fabric layer facing the absorbent core.

* * * * *